US012778817B2

(12) United States Patent
Kim et al.

(10) Patent No.: US 12,778,817 B2
(45) Date of Patent: Nov. 3, 2026

(54) METHOD FOR MANUFACTURING ABSORBENT CORE HAVING ENHANCED WET STRENGTH

(71) Applicant: LG Chem, Ltd., Seoul (KR)

(72) Inventors: Young Sam Kim, Daejeon (KR); Joo-Hwan Yoo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1181 days.

(21) Appl. No.: 15/504,158

(22) PCT Filed: Jun. 7, 2016

(86) PCT No.: PCT/KR2016/005988
§ 371 (c)(1),
(2) Date: Feb. 15, 2017

(87) PCT Pub. No.: WO2016/200112
PCT Pub. Date: Dec. 15, 2016

(65) Prior Publication Data

US 2017/0273836 A1 Sep. 28, 2017

(30) Foreign Application Priority Data

Jun. 9, 2015 (KR) ........................ 10-2015-0081162
Apr. 12, 2016 (KR) ........................ 10-2016-0044888

(51) Int. Cl.
*A61F 13/537* (2006.01)
*A61F 13/15* (2006.01)
(Continued)

(52) U.S. Cl.
CPC .... *A61F 13/5376* (2013.01); *A61F 13/15634* (2013.01); *A61F 13/53* (2013.01);
(Continued)

(58) Field of Classification Search
CPC ............ Y10T 442/611; Y10T 428/2973–2975; D01D 5/253; A61F 13/49–4963; A61F 2013/4966
See application file for complete search history.

(56) References Cited

U.S. PATENT DOCUMENTS 5,977,429 A 11/1999 Phillips et al.
6,251,322 B1 * 6/2001 Phillips ................ A61F 13/531 264/103

(Continued)

FOREIGN PATENT DOCUMENTS

CN 1234081 A 11/1999
CN 101180023 A 5/2008

(Continued)

OTHER PUBLICATIONS

International Search Report from PCT/KR2016/005988, dated Sep. 26, 2016.

(Continued)

*Primary Examiner* — Marla D Mcconnell
*Assistant Examiner* — Kevin Worrell
(74) *Attorney, Agent, or Firm* — Lerner David LLP

(57) ABSTRACT

The present invention relates to an absorbent core of an absorbent product including a liquid-permeable top sheet, an absorbent dispersion layer disposed at a lower portion of the top sheet, an absorbent core disposed at a lower portion of the absorbent dispersion layer and absorbing and retaining liquids, and a liquid-impermeable back sheet disposed at a lower portion of the absorbent core, and the absorbent core has effects of having the convenience of storage and the activity when an absorbent product prepared therefrom is worn by a user and improving liquid permeability compared to an existing absorbent core.

17 Claims, 9 Drawing Sheets

(51) Int. Cl.

| | |
|---|---|
| ***A61F 13/53*** | (2006.01) |
| ***A61L 15/60*** | (2006.01) |
| ***D01D 5/253*** | (2006.01) |
| ***D01D 5/30*** | (2006.01) |
| ***D06M 11/79*** | (2006.01) |
| ***D06M 101/32*** | (2006.01) |

(52) U.S. Cl.

CPC .............. *A61L 15/60* (2013.01); *D01D 5/253* (2013.01); *D01D 5/30* (2013.01); *D06M 11/79* (2013.01); *A61F 2013/53016* (2013.01); *A61F 2013/530255* (2013.01); *A61F 2013/530496* (2013.01); *D06M 2101/32* (2013.01)

(56) References Cited

U.S. PATENT DOCUMENTS

| | | | | |
|---|---|---|---|---|
| 6,521,339 | B1 | 2/2003 | Hansen et al. | |
| 6,657,102 | B2 | 12/2003 | Furuya et al. | |
| 2002/0173762 | A1 | 11/2002 | Ishikawa et al. | |
| 2003/0195485 | A1* | 10/2003 | Rangachari | A61F 13/15731 604/374 |
| 2005/0130540 | A1* | 6/2005 | Crane | D01F 8/02 442/364 |
| 2008/0044616 | A1* | 2/2008 | Hanao | A61F 13/15203 428/68 |
| 2008/0234645 | A1 | 9/2008 | Dodge et al. | |
| 2009/0004435 | A1* | 1/2009 | Hanao | A61F 13/53 428/156 |
| 2009/0247977 | A1* | 10/2009 | Takeuchi | A61F 13/5116 604/375 |

FOREIGN PATENT DOCUMENTS

| | | | |
|---|---|---|---|
| EP | 1862156 | A1 | 12/2007 |
| JP | 2008266812 | A | 11/2008 |
| JP | 4320311 | B2 | 8/2009 |
| KR | 20020085827 | A | 11/2002 |
| KR | 20060110474 | A | 10/2006 |
| KR | 101507287 | B1 | 3/2015 |
| WO | 9816672 | A1 | 4/1998 |

OTHER PUBLICATIONS

Chinese Search Report for Application No. 201680002359.X dated Apr. 1, 2019.

Chinese Search Report for Application No. 201680002359.X dated Jul. 16, 2019.

* cited by examiner

METHOD FOR MANUFACTURING ABSORBENT CORE HAVING ENHANCED WET STRENGTH

CROSS-REFERENCE TO RELATED APPLICATION

This application is a national phase entry under 35 U.S.C. § 371 of International Application No. PCT/KR2016/005988, filed Jun. 7, 2016, which claims priority to Korean Patent Application No. 10-2015-0081162, filed Jun. 9, 2015 and Korean Patent Application No. 10-2016-0044888, filed Apr. 12, 2016, the disclosures of which are incorporated herein by reference.

TECHNICAL FIELD

The present invention relates to a method for preparing an absorbent core of which the wet strength is reinforced, and more particularly, to an absorbent core of which the wet strength is reinforced, which is prepared from a cross non-circular cross section yarn, in which particles having specific properties are introduced into polyethylene terephthalate (PET), and a super absorbent polymer.

BACKGROUND ART

A disposable diaper is a hygiene product which absorbs a body fluid such as blood, urine, and menstrual blood, and a user can hygienically and conveniently use. In general, the disposable diaper is a product which absorbs secretions (for example, urine, blood, menstrual blood, and the like) discharged by various physiological actions of a wearer thereof, and examples of the product include a diaper, a feminine hygiene pad, a panty liner, and the like, which an infant or a person suffering from incontinence of urine uses.

The disposable diaper includes a liquid-permeable top sheet, a liquid-impermeable back sheet which forms an outer surface when worn by a user, and an absorbent core disposed between the top sheet and the back sheet as basic constituent elements. Among them, the absorbent core is a part which plays an important role to absorb secretions such as urine. The absorbent core is a means capable of absorbing and retaining liquid secretions, and the absorbent core is typically composed of a fluff pulp and a super absorbent polymer as a liquid absorbent material, a tissue which packs the fluff pulp and the super absorbent polymer, and the like, and serves a function of absorbing the body fluid passing through the liquid-permeable top sheet at a rapid speed and retaining a body fluid in order to prevent the absorbed body fluid from being again brought into contact with the skin.

In this regard, Korean Patent Application Laid-Open No. 2005-0032747 discloses a super-thin absorbent core of a disposable diaper prepared by using a fluff pulp and a preparation method thereof, but a conventional fluff pulp uses a large amount of pulp in order to serve a transfer role due to characteristics of a hydrophilic material and a plurality of pores in a diaper, and thus goes against a recent trend of a super-thin diaper.

Therefore, there is a need for developing a new concept core constituent component which can achieve a super-thin diaper while exhibiting a performance that is equivalent to or higher than that of the existing cellulose pulp.

DISCLOSURE

Technical Problem

Therefore, the present invention has been made keeping in mind the above problems encountered in the related art, and an object of the present invention is to provide an absorbent core of which the wet strength is reinforced, which is prepared from a cross non-circular cross section yarn, in which particles having specific properties are introduced into polyethylene terephthalate (PET), and a super absorbent polymer.

Another object thereof is to provide a super-thin absorbent product which is a recent trend by using the absorbent core.

Technical Solution

The present invention provides an absorbent core of an absorbent product including a liquid-permeable top sheet, an absorbent dispersion layer disposed at a lower portion of the top sheet, an absorbent core disposed at a lower portion of the absorbent dispersion layer and absorbing and retaining liquids, and a liquid-impermeable back sheet disposed at a lower portion of the absorbent core, in which the absorbent core includes a cross non-circular cross section yarn prepared by mixing an aqueous dispersion including particles having characteristics of i) a BET specific surface area of 300 to 1,500 $m^2/g$ and ii) a porosity of 50% or more with polyethylene terephthalate (PET) and a super absorbent polymer.

Further, the present invention provides a method for preparing an absorbent core, the method including: 1) adding an aqueous dispersion including particles having characteristics of i) a BET specific surface area of 300 to 1,500 $m^2/g$ and ii) a porosity of 50% or more to polyethylene terephthalate to prepare a cross non-circular cross section yarn;

2) depositing the cross non-circular cross section yarn and a super absorbent polymer to form an absorbent core outer form; and 3) compressing the absorbent core outer form.

In addition, the present invention provides an absorbent product including the absorbent core.

Advantageous Effects

The absorbent core provided by the present invention has an advantage of securing the convenience of storage and the activity when an absorbent product prepared therefrom is worn by a user because a super-thin absorbent product can be made while exhibiting a performance that is equivalent to or higher than that of the existing cellulose pulp.

Further, the absorbent core provided by the present invention includes particles having specific properties when a cross non-circular cross section yarn is prepared, thereby improving liquid permeability because the porosity is increased and high hydrophobicity is imparted to the absorbent core.

BEST MODE

Hereinafter, the present invention will be described in detail.

The present invention relates to an absorbent core of an absorbent product including a liquid-permeable top sheet, an absorbent dispersion layer disposed at a lower portion of the top sheet, an absorbent core disposed at a lower portion of the absorbent dispersion layer and absorbing and retaining liquids, and a liquid-impermeable back sheet disposed at a lower portion of the absorbent core, in which the absorbent core includes a cross non-circular cross section yarn prepared by mixing an aqueous dispersion including particles having characteristics of i) a BET specific surface area of 300 to 1,500 $m^2/g$ and ii) a porosity of 50% or more with polyethylene terephthalate (PET) and a super absorbent polymer.

Further, the present invention relates to a method for preparing an absorbent core, the method including: 1) adding an aqueous dispersion including particles having the following characteristics of i) a BET specific surface area of 300 to 1,500 $m^2/g$ and ii) a porosity of 50% or more to polyethylene terephthalate to prepare a cross non-circular cross section yarn;

2) depositing the cross non-circular cross section yarn and a super absorbent polymer to form an absorbent core outer form; and 3) compressing the absorbent core outer form.

The absorbent core constitutes an absorbent product including a liquid-permeable top sheet, an absorbent dispersion layer disposed at a lower portion of the top sheet, an absorbent core disposed at a lower portion of the absorbent dispersion layer and absorbing and retaining liquids, and a liquid-impermeable back sheet disposed at a lower portion of the absorbent core.

The 'polyethylene terephthalate (PET)' is composed of a polymerized unit of a monomeric ethylene terephthalate, and has a repeating unit of $C_{10}H_8O_4$. The polyethylene terephthalate (PET) has excellent heat resistance, rigidity, electrical properties, and the like, and the ultimate strength is only slightly reduced even though being placed at high temperature for a long period of time. The polyethylene terephthalate (PET) belongs to crystalline plastics, and thus has good resistance to oils such as diesel oil. However, the polyethylene terephthalate (PET) has an ester bond in the molecular chain thereof, and thus has an easily changeable property when an article molded therefrom is dipped in acid or alkali at high temperature for a long period of time.

In the present invention, polyethylene terephthalate is used in the form of a cross non-circular cross section yarn.

The 'cross non-circular cross section yarn' means a yarn in which the cross-section state of the yarn is modified by changing the shape of a nozzle used when a synthetic fiber is spun from a typical circular shape to a cross shape.

Figure 1:
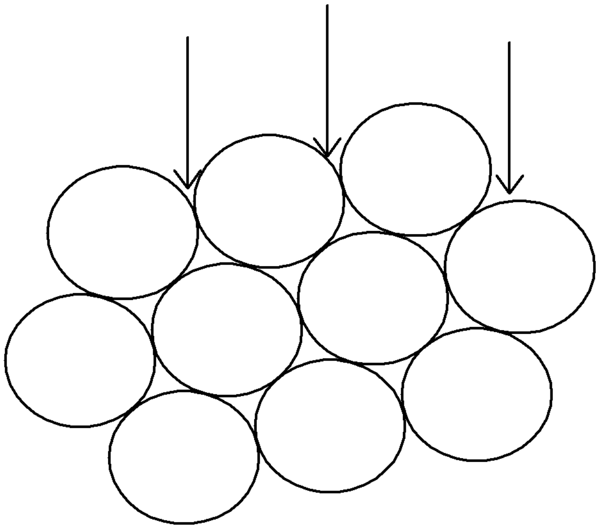
FIG. 1 is a schematic view of a cellulose absorbent core in the related art.
Figure 2:
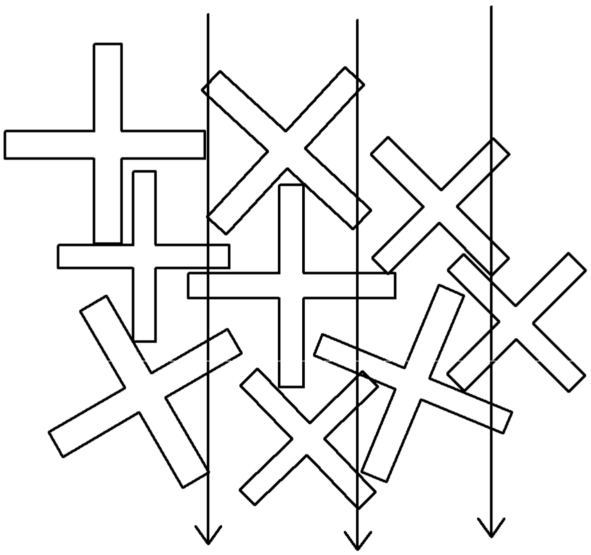
FIG. 2 is a schematic view of a non-circular cross-section yarn absorbent core of the present invention.
Figure 3:
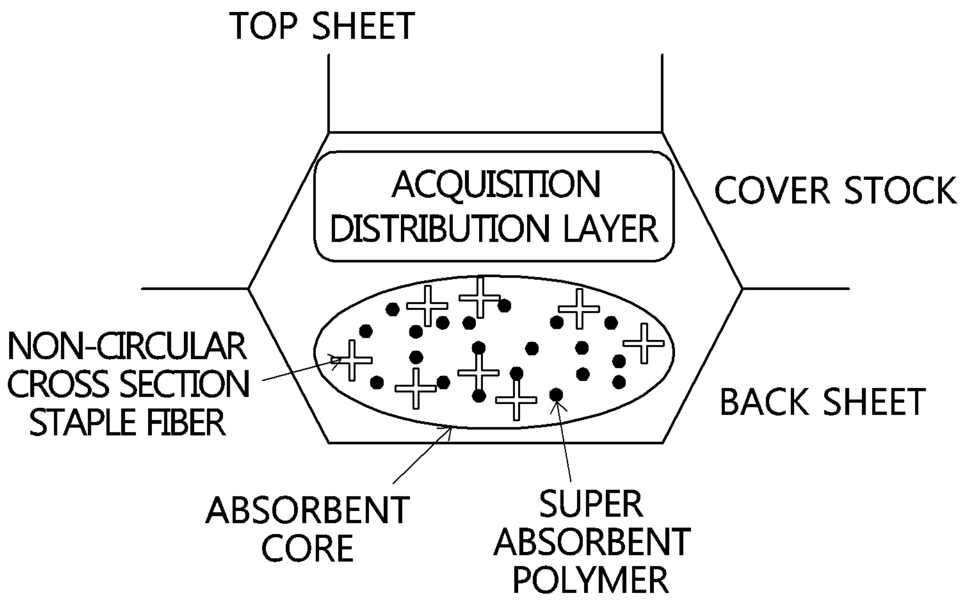
FIG. 3 is a schematic view of a structure of an absorbent product including the non-circular cross-section yarn absorbent core of the present invention.
Figure 4:
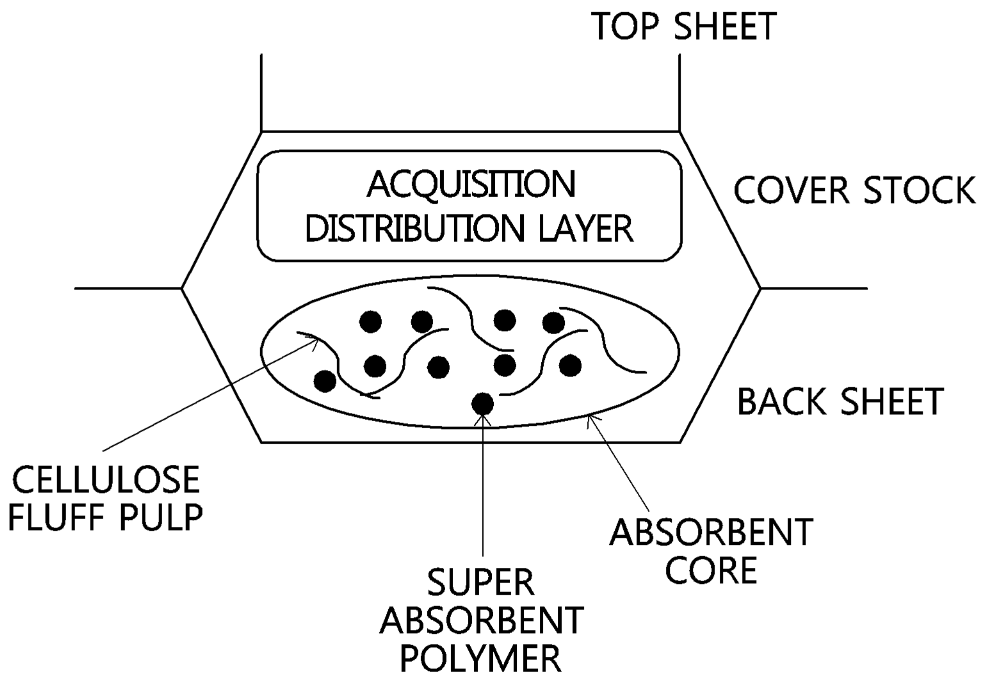
FIG. 4 is a schematic view of a structure of an absorbent product including a cellulose absorbent core in the related art.

Since the existing absorbent core has a circular cross section and has a problem in that a liquid does not easily move due to the structural limitation, an absorbent product is prepared by a method of using a large amount of pulp to secure the porosity (FIG. 1). However, the present invention improves the liquid permeability and the mobility of a liquid by preparing a core having a maximized porosity using a biodegradable cross non-circular cross section (NCCS) yarn. Further, even though a small amount of fiber is used, the porosity may be sufficiently secured, thereby expecting weight reduction and thickness reduction effects (FIG. 2).

A cross non-circular cross section yarn fiber included in the absorbent core of the present invention is prepared by adding an aqueous dispersion including particles having characteristics of i) a BET specific surface area of 300 to 1,500 $m^2/g$ and ii) a porosity of 50% or more to polyethylene terephthalate.

As the particles having the characteristics are included, the liquid permeability is improved because the porosity is increased and high hydrophobicity is imparted to the absorbent core.

In an exemplary embodiment of the present invention, it is preferred that the particles have a particle size of 2 nm to 50 μm or are super-hydrophobic while having a contact angle with respect to water of 125° or more, it is more preferred that the particles have both the particle size and contact angle characteristics, but the particles are not limited thereto.

In an exemplary embodiment of the present invention, the aqueous dispersion may include the particles, water, and an organic solvent, the organic solvent may be one or more selected from the group consisting of methanol, ethanol, isopropyl alcohol (IPA), and acetone, and it is more preferred to use isopropyl alcohol (IPA).

When the cross non-circular cross section yarn of the present invention is prepared, the introduced particles have a particle size of 2 nm to 50 μm. Further, the particles may have a BET specific area of 300 to 1,500 $m^2/g$, preferably 500 to 1,500 $m^2/g$, and more preferably 700 to 1,500 $m^2/g$. In addition, the particles may have super-hydrophobicity with a contact angle with respect to water of 125° or more, preferably 140° or more, and more preferably 145° or more. Furthermore, the particles may have a porosity of 50% or more, preferably 90% or more.

For the particles of the present invention, the component thereof not limited is not limited as long as the component is a material having the characteristics of i) and ii), and specifically, it is possible to use carbon, an inorganic oxide such as silica ($SiO_2$), alumina, and titania ($TiO_2$), an inorganic compound, an organic polymer, an ion exchange resin, a metal, a metal salt, and the like, but the component is not limited thereto, and it is preferred to use silica ($SiO_2$).

The particles are characterized to be included in an amount of 1 to 25 parts by weight based on 100 parts by weight of a mixed solution of water and an organic solvent. When particles are included in the range, dispersion proceeds well, and there is no gelation due to dispersion instability during the storage for a long period of time. Accordingly, since an auxiliary agent such as an additive, a pH adjusting agent, a surfactant, or a stabilizer may not be included in order to prevent the gelation, it is possible to maintain inherent super-hydrophobic and porous properties of the particles when the particles are dried. Accordingly, there is an advantage in that the auxiliary agent need not be removed through the pre-treatment prior to the process, and the particles may be directly applied to the process.

Furthermore, after the aqueous dispersion is added thereto, the speed at which the mixture is mixed is preferably 200 to 3,000 rpm. There is a problem in that when the mixing speed is less than 200 rpm, the effects resulting from the mixing are not sufficiently exhibited, and when the mixing speed is more than 3,000 rpm, the particles are excessively ground.

Further, it is preferred that after the aqueous dispersion including the particles is added to the cross non-circular cross section yarn, the mixture is mixed for 10 seconds to 3 minutes. There is a problem in that when the mixing time is less than 10 seconds, the effects resulting from the mixing are not sufficiently exhibited, and when the mixing time is more than 3 minutes, the particles are excessively ground.

In an exemplary embodiment of the present invention, it is preferred that the absorbent core includes a cross non-circular cross section yarn and a super absorbent polymer at a ratio of 1:5 to 5:1, but the ratio is not limited thereto.

In an exemplary embodiment of the present invention, the absorbent product may include a diaper, toilet training pants, absorbent underpants, a product for adult incontinence, a feminine hygiene product such as a hygiene pad, a tampon, and a panty liner, a wound care product such as a wound dressing, other products, and the like, but the absorbent product is preferably a diaper.

The absorbent product is a product which absorbs a body fluid such as blood, urine, and menstrual blood, and a user can hygienically and conveniently use.

The absorbent product usually includes a liquid-permeable top sheet which is directly brought into contact with the skin of a wearer when the product is worn by the wearer, a liquid-impermeable back sheet which forms an outer surface when the product is worn by the wearer, an absorbent core disposed between the top sheet and the back sheet, a leg flap composed of an elastomer, and a fastening means as basic constituent elements.

Among the constituent elements as described above, the top sheet is composed of materials which are usually soft to touch and do not irritate the skin of the wearer, and particularly, the top sheet should have physical properties that allow liquid body secretions to rapidly pass through the absorbent core. As a top sheet having these physical properties, a suitable top sheet is prepared from a wide variety of materials such as a porous plastic film, a natural fiber, a synthetic fiber, or a mixture of natural and synthetic fibers and used.

The absorbent core is a means capable of absorbing and retaining liquid secretions, and serves a function of absorbing the body fluid passing through the liquid-permeable top sheet at a rapid speed and retaining a body fluid in order to prevent the absorbed body fluid from being again brought into contact with the skin. The absorbent core is configured so as to have a size, a shape (for example, rectangular shape, an hourglass shape, and the like), a structure, an absorption ability, and the like suitable for a wearer from an infant to an adult, and the absorbent core is attached and fixed on the back sheet by any known attaching means.

The back sheet is impermeable to liquids, and thus allows body secretions absorbed and contained in the absorbent core not to contaminate and wet a product such as a wearer's clothing or bed sheet, which is directly brought into contact with a diaper. It is preferred that the back sheet is impermeable to liquids and permeable to gases. As a back sheet having these properties, a plastic film has been usually used, and recently, a material in which a non-woven fabric is adhered to a polyethylene film has been widely used.

The leg flap is disposed adjacent to each perpendicular edge such that a diaper is worn and fixed on the legs of a wearer.

The fastening means serves a function capable of maintaining the worn state as it is by wearing a disposable diaper on a human body. As the fastening means, a pressure-sensitive adhesive tape tap or a fastening member such as a hook or a loop has been widely used.

Various members, which are each constituent element constituting the diaper, are adhered and fixed by a high temperature melt adhesive, thermal bonding or other adhesion methods, which are already well-known in the diaper field, thereby forming a diaper.

The conventional absorbent core has been prepared by a method including: evenly or intentionally unevenly dispersing a super absorbent polymer prepared by using a fluff pulp composed of ground wooden pulp on a fibrous web, a starch graft copolymer, a cross-linked carboxymethyl cellulose derivative, a modified hydrophilic acrylate, and the like, adding moisture thereto in order to improve the strength (integrity) of the absorbent core, and then compressing the resulting product.

Recently, as diaper have been constantly more and more ergonomically developed, diapers tend to have a weight reduction and a small thickness. This is because consumers prefer a thin and light diaper due to advantages in that the diaper improves the air permeability to increase the freshness due to the weight reduction and small thickness when being worn, prevents side effects such as itching and rash when worn for a long period of time due to the excellent air permeability, and is conveniently carried and kept, and the like.

Thus, the absorbent product of the present invention improves the liquid permeability and the mobility of liquids by replacing a cellulose fluff pulp contained in a core of the existing absorbent product with a cross non-circular cross section yarn fiber to prepare an absorbent core having a maximized porosity.

The super absorbent polymer used in the absorbent core of the present invention is prepared by the steps and methods usually used in the art.

The 'super absorbent polymer' may absorb about 15 folds or more of the weight, preferably about 25 folds or more of the weight in water. The super absorbent polymer may be selected from natural, synthetic, and modified natural polymers, and the like. Further, the super absorbent polymer may be an organic compound including an inorganic material such as silica gel, or a natural material such as agar, pectin, and guar gum, and a synthetic material such as a synthetic hydrogel polymer. Examples of the hydrogel polymer include an alkali metal salt such as polyacrylic acid; a polyacrylamide; a polyvinyl alcohol; an ethylene maleic anhydride copolymer; a polyvinyl ether; a hydroxypropyl cellulose; a polyvinyl morpholinone; a polymer and a copolymer of vinyl sulfonic acid, a polyacrylate, a polyacrylamide, a polyvinyl pyridine, and the like. Examples of other suitable polymers include a hydrolyzed acrylonitrile grafted starch, an acrylic acid grafted starch, an isobutylene maleic anhydride copolymer, and a mixture thereof. The hydrogel polymer is preferably weakly crosslinked, and thus renders a material substantially water insoluble. The cross-linkage may be produced by, for example, a covalent bond by photo irradiation, an ionic bond, a van der Waals bond, or a hydrogen bond. The super absorbent material may be in any form suitable for use in an absorbent structural body including a particle, a fiber, a flake, a sphere, and the like.

In an exemplary embodiment of the present invention, it is preferred that the absorbent core includes a cross non-circular cross section yarn and a super absorbent polymer in an equivalent weight, but the absorbent core is not limited thereto.

In an exemplary embodiment of the present invention, the absorbent product may include a diaper, toilet training pants, absorbent underpants, a product for adult incontinence, a feminine hygiene product such as a hygiene pad, a tampon, and a panty liner, a wound care product such as a wound dressing, other products, and the like, but the absorbent product is preferably a diaper.

The absorbent product is a product which absorbs a body fluid such as blood, urine, and menstrual blood, and a user can hygienically and conveniently use.

The absorbent product usually includes a liquid-permeable top sheet which is directly brought into contact with the skin of a wearer when the product is worn by the wearer, a liquid-impermeable back sheet which forms an outer surface when the product is worn by the wearer, an absorbent core disposed between the top sheet and the back sheet, a leg flap composed of an elastomer, and a fastening means as basic constituent elements.

Among the constituent elements as described above, the top sheet is composed of materials which are usually soft to touch and do not irritate the skin of the wearer, and particularly, the top sheet should have physical properties that allow liquid body secretions to rapidly pass through the absorbent core. As a top sheet having these physical properties, a suitable top sheet is prepared from a wide variety of materials such as a porous plastic film, a natural fiber, a synthetic fiber, or a mixture of natural and synthetic fibers and used.

The absorbent core is a means capable of absorbing and retaining liquid secretions, and serves a function of absorbing the body fluid passing through the liquid-permeable top sheet at a rapid speed and retaining a body fluid in order to prevent the absorbed body fluid from being again brought into contact with the skin. The absorbent core is configured so as to have a size, a shape (for example, rectangular shape, an hourglass shape, and the like), a structure, an absorption ability, and the like suitable for a wearer from an infant to an adult, and the absorbent core is attached and fixed on the back sheet by any known attaching means.

The back sheet is impermeable to liquids, and thus allows body secretions absorbed and contained in the absorbent core not to contaminate and wet a product such as a wearer's clothing or bed sheet, which is directly brought into contact with a diaper. It is preferred that the back sheet is impermeable to liquids and permeable to gases. As a back sheet having these properties, a plastic film has been usually used, and recently, a material in which a non-woven fabric is adhered to a polyethylene film has been widely used.

The leg flap is disposed adjacent to each perpendicular edge such that a diaper is worn and fixed on the legs of a wearer.

The fastening means serves a function capable of maintaining the worn state as it is by wearing a disposable diaper on a human body. As the fastening means, a pressure-sensitive adhesive tape tap or a fastening member such as a hook or a loop has been widely used.

Various members, which are each constituent element constituting the diapers, are adhered and fixed by a high temperature melt adhesive, thermal bonding or other adhesion methods, which are already well-known in the diaper field, thereby forming a diaper.

The conventional absorbent core has been prepared by a method including: evenly or intentionally unevenly dispersing a super absorbent polymer prepared by using a fluff pulp composed of ground wooden pulp on a fibrous web, a starch graft copolymer, a cross-linked carboxymethyl cellulose derivative, a modified hydrophilic acrylate, and the like, adding moisture thereto in order to improve the strength (integrity) of the absorbent core, and then compressing the resulting product.

Recently, as being constantly more and more ergonomically developed, diapers tend to have a weight reduction and a small thickness. This is because consumers prefer a thin and light diaper due to advantages in that the diaper improves the air permeability to increase the freshness due to the weight reduction and small thickness when being worn, prevents side effects such as itching and rash when worn for a long period of time due to the excellent air permeability, and is conveniently carried and kept, and the like.

Thus, the absorbent product of the present invention improves the liquid permeability and the mobility of liquids by replacing a cellulose fluff pulp contained in a core of the existing absorbent product with a cross non-circular cross section yarn fiber to prepare an absorbent core having a maximized porosity.

The super absorbent polymer used in the absorbent core of the present invention is prepared by the steps and methods usually used in the art.

MODE FOR INVENTION

Hereinafter, the present invention will be described in more detail with reference to non-limiting Examples. The exemplary embodiments of the present invention are provided only for illustration, and the scope of the present invention is not limited to the exemplary embodiments thereof. The scope of the present invention is described in the claims, and includes meanings equivalent to the claims and all modifications therein. Further, in the following Examples and Comparative Examples, "%" and "parts" representing the content is a mass standard unless otherwise particularly mentioned.

EXAMPLES

Example 1

Preparation of Absorbent Core (1) Preparation of Cross Non-Circular Cross Section Yarn 1 wt % of an aqueous dispersion including 10 wt % of a silica aerogel (AeroZel™, manufactured by JIOS) was added to a cross non-circular cross section yarn (COOLERVER™ manufactured by HUBIS) prepared by polyethylene terephthalate, and then the resulting mixture was stirred by a Ploughshare mixer (JS tech) to prepare a cross non-circular cross section yarn containing a silica aerogel. An aqueous silica aerogel dispersion was prepared at a ratio of isopropyl alcohol:water:silica aerogel=45:45:10 wt %.

(2) Preparation of Absorbent Core

An absorbent core was prepared by a process of evenly spraying a super absorbent polymer on a cross non-circular cross section yarn, then using a core depositing machine to repeatedly perform the deposition four times, and compressing the resulting product with water. The ratio of the cross non-circular cross section yarn to the super absorbent polymer is 55 wt % to 45 wt %. The preparation process is illustrated in FIG. 8A through 8E.

Comparative Example 1

Cellulose Pulp Absorbent Core

An absorbent core was prepared in the same manner as in Example 1, except that a cellulose pulp was used instead of the cross non-circular cross section yarn.

Comparative Example 2

Absorbent Core Not Containing Particles

An absorbent core was prepared in the same manner as in Example 1, except that an aqueous dispersion including the silica aerogel (AeroZel™, manufactured by JIOS) of Example 1 was not mixed.

Test Examples

In order to evaluate physical properties of the absorbent cores according to Example 1 and Comparative Examples 1 and 2, an experiment to be described below was performed.

Test Example 1

Strike Thru Experiment

Figure 5:
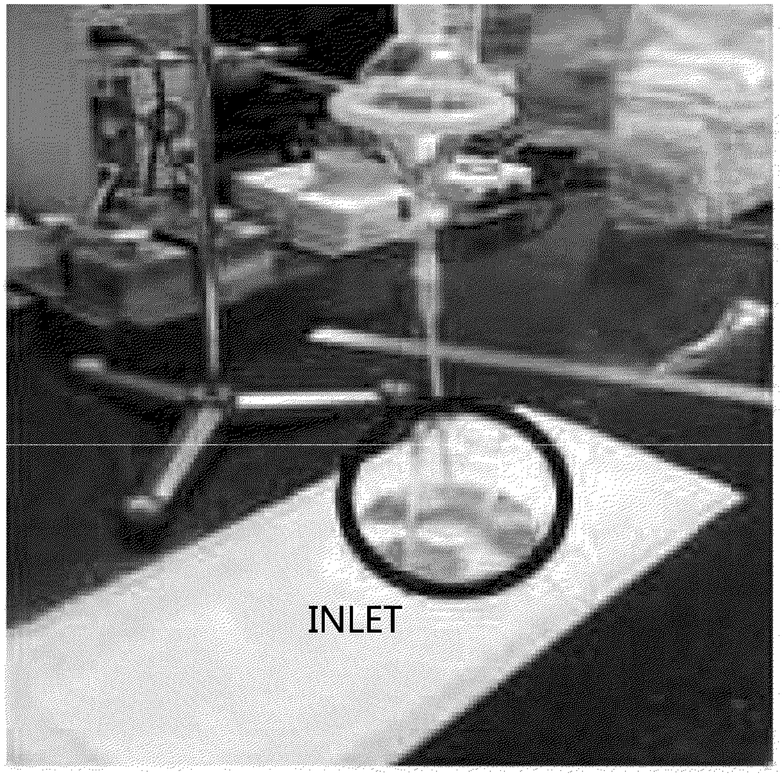
FIGS. 5 and 6 illustrate a test procedure of Test Example 1.
Figure 6:
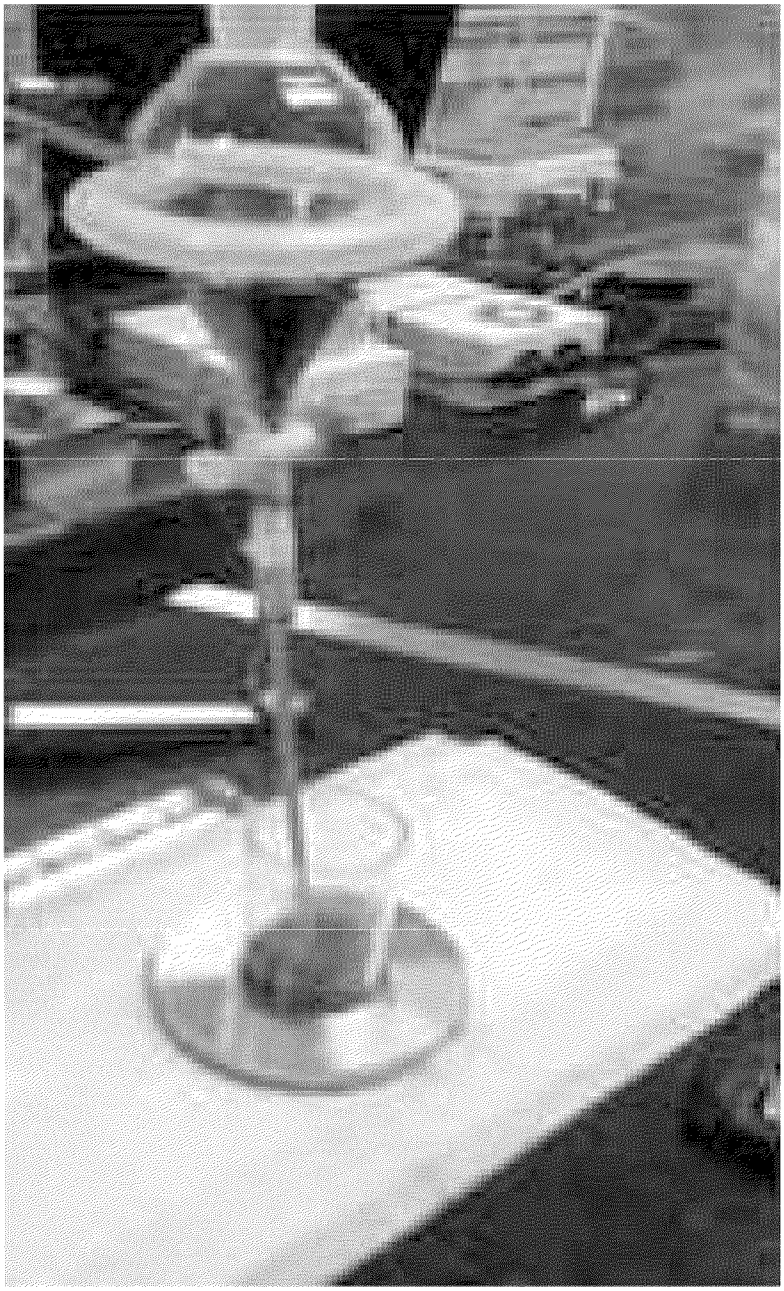
Figure 7:
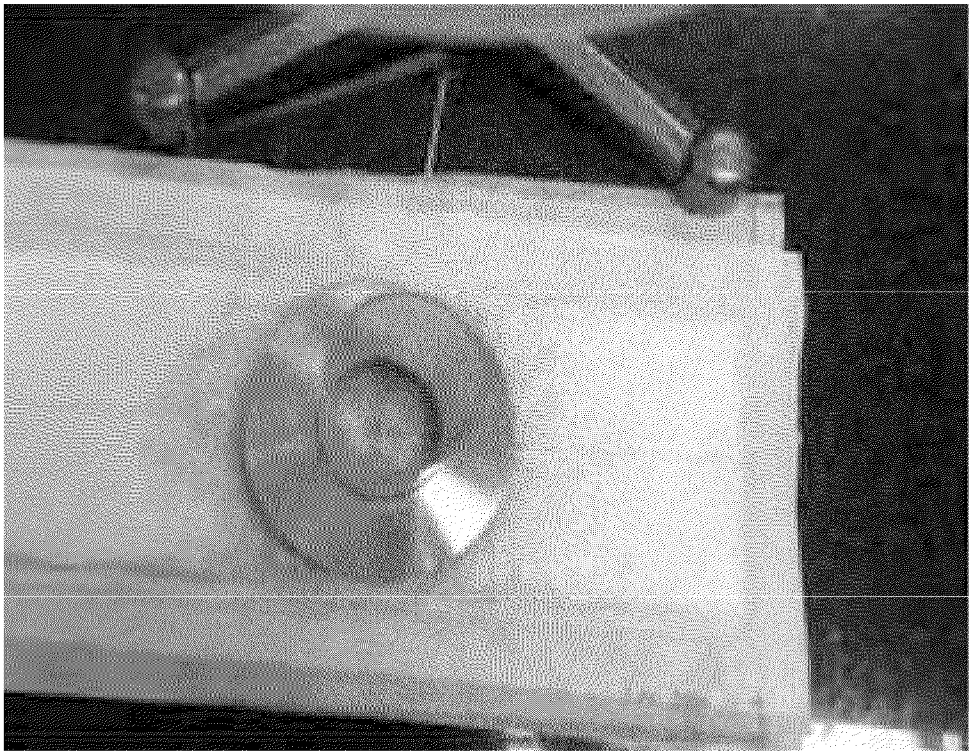
FIG. 7 illustrates a test result of Test Example 1.
Figure 8A:
FIG. 8A through 8E illustrates a preparation procedure of an absorbent core.
Figure 8B:
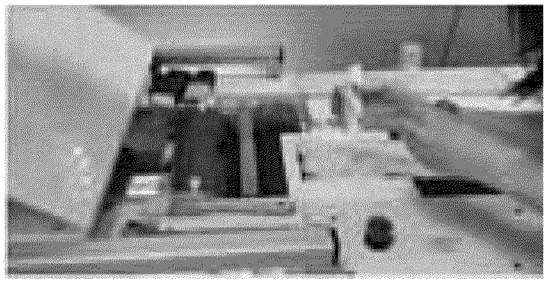
Figure 8C:
Figure 8D:
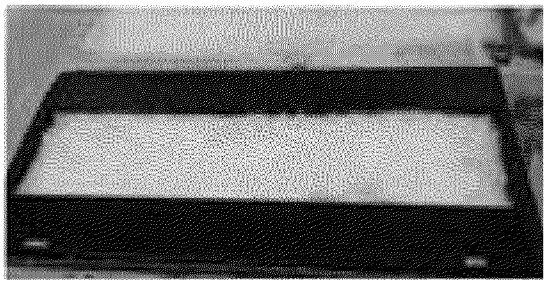
Figure 8E:

The time from an instant when a brine was added through an injection port to the absorbent cores prepared in Examples 1 and Comparative Examples 1 and 2 until an instant when the brine was completely absorbed in the absorbent cores was measured. The measurement was made repeatedly three times for the same sample. A fast time indicates that the brine has high liquid permeability in which the brine passes through the absorbent core. The test procedure is illustrated in FIGS. 5 to 7. The results are shown in Table 1.

TABLE 1

| Measured physical properties | | Comparative Example 1 | Comparative Example 2 | Example 1 |
|---|---|---|---|---|
| Strike thru (sec) | First trial | 59 | 57 | 56 |
| | Second trial | 63 | 60 | 57 |
| | Third trial | 83 | 74 | 66 |

As in Table 1, it can be seen that in the case of the absorbent core according to the present invention, the liquid permeability is improved.

The invention claimed is:

1. An absorbent core of an absorbent product consisting of:

a cross non-circular cross section yarn and a super absorbent polymer, wherein the super absorbent polymer is sprayed on the cross non-circular cross section yarn to form an absorbent core outer form, wherein the cross non-circular cross section yarn comprises particles and polyethylene terephthalate (PET), wherein the particles have characteristics of i) a BET specific surface area of 300 to 1,500 $m^2/g$ and ii) a porosity of 50% or more, wherein the cross non-circular cross section yarn is prepared by mixing an aqueous dispersion comprising the particles and the PET, wherein the aqueous dispersion comprises water and an organic solvent, and the particles are comprised in an amount of 1 to 25 parts by weight based on 100 parts by weight of the water and the organic solvent, wherein the cross non-circular cross section yarn and the super absorbent polymer sprayed on the cross non-circular section yarn are in a ratio of 1:5 to 5:1 by weight in the absorbent core, and wherein the particles are super-hydrophobic while having a contact angle with respect to water of 125° or more.

2. The absorbent core of claim 1, wherein the particles have a particle size of 2 nm to 50 μm.

3. The absorbent core of claim 1, wherein the particles have a BET specific surface area of 500 to 1,500 $m^2/g$.

4. The absorbent core of claim 3, wherein the particles have a BET specific surface area of 700 $m^2/g$ to 1,500 $m^2/g$.

5. The absorbent core of claim 1, wherein the particles are super-hydrophobic while having a contact angle with respect to water of 140° or more.

6. The absorbent core of claim 5, wherein the particles are super-hydrophobic while having a contact angle with respect to water of 145° or more.

7. The absorbent core of claim 1, wherein the particles have a porosity of 90% or more.

8. The absorbent core of claim 1, wherein the organic solvent is one or more selected from a group consisting of methanol, ethanol, isopropyl alcohol (IPA), and acetone.

9. The absorbent core of claim 8, wherein the organic solvent is isopropyl alcohol (IPA).

10. The absorbent core of claim 1, wherein the particles are one or more selected from a group consisting of silica ($SiO_2$), alumina, carbon, and titania ($TiO_2$).

11. The absorbent core of claim 10, wherein the particles are silica ($SiO_2$).

12. The absorbent core of claim 1, wherein the absorbent core comprises a cross non-circular cross section yarn and a super absorbent polymer in an equivalent weight.

13. The absorbent core of claim 1, wherein the absorbent product is a diaper.

14. An absorbent product comprising the absorbent core of claim 1.

15. The absorbent core of claim 1, wherein the cross non-circular cross section yarn and the super absorbent polymer are in a ratio of 5.5:4.5 to 5:5 by weight.

16. The absorbent core of claim 1, wherein the aqueous dispersion comprises water and an organic solvent in an equivalent weight, and the particles in an amount of 11.11 to 25 parts by weight based on 100 parts by weight of the water and the organic solvent.

17. The absorbent product of claim 14, comprising a liquid-permeable top sheet, an absorbent dispersion layer disposed at a lower portion of the top sheet, the absorbent core disposed at a lower portion of the absorbent dispersion layer and absorbing and retaining liquids, and a liquid-impermeable back sheet disposed at a lower portion of the absorbent core.

* * * * *